United States Patent [19]
Kroner et al.

[11] Patent Number: 5,540,663
[45] Date of Patent: Jul. 30, 1996

[54] USE OF POLYACETALS FOR PREPARING COMPOSTABLE MOLDINGS, AS COATING AND AS ADHESIVE

[75] Inventors: Matthias Kroner, Eisenberg; Gunnar Schornick, Neuleiningen; Karl-Heinz Schumacher, Neustadt; Eckehardt Wistuba, Bad Durkheim, all of Germany

[73] Assignee: BASF Aktiengesellschaft, Ludwigshafen, Germany

[21] Appl. No.: 530,125

[22] PCT Filed: Apr. 18, 1994

[86] PCT No.: PCT/EP94/01200

§ 371 Date: Oct. 12, 1995

§ 102(e) Date: Oct. 12, 1995

[87] PCT Pub. No.: WO94/24189

PCT Pub. Date: Oct. 27, 1994

[30] Foreign Application Priority Data

Apr. 20, 1993 [DE] Germany .......................... 43 12 753.3

[51] Int. Cl.⁶ ..................................... A61F 13/15
[52] U.S. Cl. .......................... 428/221; 525/472; 604/366
[58] Field of Search ............................ 525/472; 428/221; 604/366

[56] References Cited

U.S. PATENT DOCUMENTS

| | | | |
|---|---|---|---|
| 4,549,010 | 11/1985 | Sparer et al. | 528/361 |
| 4,806,598 | 2/1989 | Morman | 525/63 |
| 4,828,911 | 5/1989 | Morman | 428/288 |
| 4,857,251 | 8/1989 | Nohr et al. | 264/103 |
| 4,920,168 | 4/1990 | Nohr et al. | 524/188 |
| 5,455,108 | 10/1995 | Quincy, III et al. | 428/266 |

FOREIGN PATENT DOCUMENTS

| | | |
|---|---|---|
| 4142130 | 6/1993 | Germany . |
| 91/11466 | 8/1991 | WIPO . |

OTHER PUBLICATIONS

Acc. Chem. Res. 1993, 26, 105–110, Directions for Environmentally Biodegradable Polymer Research, Swift.

*Primary Examiner*—Samuel A. Acquah
*Attorney, Agent, or Firm*—Keil & Weinkauf

[57] ABSTRACT

Use of polyacetals containing acetaldehyde acetal units, and of mixtures of these polyacetals with fillers, for preparing compostable moldings, as coating and as adhesive, and also diapers with an outer layer comprising polyacetals containing acetaldehyde acetal units in the form of a compostable film or a compostable coating.

1 Claim, No Drawings

USE OF POLYACETALS FOR PREPARING COMPOSTABLE MOLDINGS, AS COATING AND AS ADHESIVE

This application is a 371 of PCT/EP94/01200 filed Apr. 18, 1994.

The present invention relates to the use of polyacetals containing acetaldehyde acetal units, and of mixtures of these polyacetals with fillers, for preparing compostable moldings, as coating and as adhesive, and to diapers with an outer layer comprising polyacetals containing acetaldehyde acetal units in the form of a compostable film or a compostable coating..

Thermoplastic materials, such as polyethylene, polypropylene and polystyrene, which are customarily used for manufacturing packaging, are not biodegradable. The used packaging materials are disposed of by recycling, incineration with energy recovery, or landfilling. Because of the increasing amounts of refuse, however, the composting of refuse is becoming more and more important. Yet the plastics mentioned above are not compostable. For instance, diapers with a polyethylene film as outer layer are not readily compostable. First the film has to be separated from the other constituents of the diaper in an additional operation, or the diaper has to be mechanically comminuted. But mechanical comminution leaves comparatively large pieces of film which are undesirable in biowaste and later also in the soil.

Journal of Polymer Science: Polymer Letters Edition 18, (1980), 293–297, discloses the preparation of polyacetals by acid-catalyzed addition of polyols to divinyl ethers. For instance, polyaddition of trans-1,4-cyclohexanedimethanol to butanediol divinyl ether under the catalytic action of p-toluenesulfonic acid produces a polyacetal having a molecular weight of 200,000. The polyacetals described are used in medicine for the controlled release of active compounds.

German Patent Application P 4142130.2, unpublished at the priority date of the present invention, discloses the use of polyacetals which are obtainable by cationically initiated polyaddition of divinyl ethers and dihydroxy compounds and also, optionally, monohydroxy compounds in low-phosphate and phosphate-free detergents and cleaners. It also discloses polyacetals which are obtainable by cationically initiated polyaddition of divinyl ethers and dihydroxy compounds and subsequent addition of monohydroxy compounds to 5–95% of the vinyl ether groups in the polyacetal, so that the polyacetals formed have vinyl ether groups.

It is an object of the present invention to provide materials for preparing compostable or rottable moldings, coatings or adhesions and also diapers which can be composted.

We have found that this object is achieved according to the present invention by the use of polyacetals containing acetaldehyde acetal units, and of mixtures of these polyacetals with fillers, for preparing compostable moldings, as coating and as adhesive.

The present invention also provides diapers with an outer layer comprising polyacetals containing acetaldehyde acetal units in the form of a compostable film or a compostable coating.

Preferred acetaldehyde acetal polyacetals are obtainable by cationically initiated polyaddition of monovinyl ethers of dihydric alcohols or by cationically initiated polyaddition of (a) dihydric alcohols, which may optionally be replaced by up to 50 mol % of other alcohols, and (b) divinyl ether or divinyl ethers of dihydric alcohols, in which case the divinyl ethers mentioned may be optionally replaced by up to 50 mol % of other vinyl ethers.

For example, polyaddition of diols and divinyl ethers gives rise to polyacetals in which the underlying diols are linked together as repeat units via acetaldehyde acetal units. The acetaldehyde acetal units in such polymers act as predetermined breaking points, at which the polymers can be cleaved, enzymatically or hydrolytically, with molecular weight reduction, into readily biodegradable polymer fragments or diols. The enzymatic attack on these polyacetals comes from microorganisms, for example bacteria or fungi. Hydrolytic degradation is obtained on lowering the pH of the medium surrounding the polyacetals. If the pH is reduced to below 7, for example owing to biological processes in the compost or in the soil or due to addition of acids, the polyacetals can be composted, or rot. Even the acidity of the carbon dioxide present in the Earth's atmosphere is sufficient to bring about an acid-initiated hydrolysis of the polyacetals. Hydrolysis of the polyacetals gives rise essentially to acetaldehyde and diols which underlie the divinyl ethers of component (b) and also come from component (a). Acetaldehyde and diols are fully biodegradable under composting conditions.

Suitable acetaldehyde acetal polyacetals are the polyacetals described in the above-cited references and preferably also the polyacetals described in German Patent Applications P 21 30 428.4, P 41 42 130.2, P 42 33 340.7 and P 42 37 337.9, each unpublished at the priority date of the present invention. The polyacetals described in said applications are essentially used in low-phosphate and phosphate-free detergents and cleaners or in dishwashing compositions. They are also suitable for use as dispersants. Preferred polyacetals are obtainable by cationically initiated polyaddition of (a) dihydric alcohols, which may optionally be replaced by up to 50 mol % of other alcohols, and (b) divinyl ether or divinyl ethers of dihydric alcohols, in which case the divinyl ethers mentioned may be optionally replaced by up to 50 mol % of other vinyl ethers, or by cationically initiated polyaddition of monovinyl ethers of dihydric alcohols.

Suitable dihydric alcohols for use as component (a) include all aliphatic and aromatic diols having more than 2 carbon atoms, for example alkylene glycols and polyalkylene glycols such as ethylene glycol, diethylene glycol, propylene glycol, dipropylene glycol, polypropylene glycol, polytetrahydrofuran, butanediol, hexanediol, cyclohexanedimethanol, cyclohexanediol, diethyl tartrate, bisphenol A, bis(hydroxyphenyl) sulfone, bis(hydroxyphenyl) ketone, hydroxylated fatty acid esters, oligomeric or polymeric esters of dicarboxylic acids and diols having alcohol end groups.

To prepare these oligomeric or polymeric esters with alcohol end groups, dicarboxylic acids or hydroxydicarboxylic acids can be reacted with diols. Examples of suitable dicarboxylic acids are aromatic dicarboxylic acids such as terephthalic acid, phthalic acid or isophthalic acid, or else aliphatic dicarboxylic acids such as $C_2$- to $C_{10}$-dicarboxylic acids, in particular oxalic acid, succinic acid or adipic acid. However, it is also possible to use glycolic acid or lactic acid. Suitable diols include not only aromatic but also aliphatic diols. Particular preference is given to $C_2$- to $C_{10}$-alkylenediols, of which ethylene glycol, 1,2-propylene glycol, 1,3-propylene glycol, 1,2-butanediol, 1,4-butanediol and 1,6-hexanediol are particularly suitable. It is, of course, also possible to use cycloaliphatic diols such as cyclohexanedimethanol. An example of an aromatic diol is bisphenol A. It is, of course, also possible to use mixtures of different dicarboxylic acids or different diols for preparing the oligomeric or polymeric esters with alcohol end groups.

Very particularly preferred alcohol end group oligomeric or polymeric esters are constructed from the following monomeric units:

succinic acid and 1,4-butanediol,
succinic acid and ethylene glycol,
succinic acid and 1,6-hexanediol,
adipic acid and 1,4-butanediol,
adipic acid and ethylene glycol,
adipic acid and 1,6-hexanediol,
terephthalic acid and 1,4-butanediol,
terephthalic acid and ethylene glycol,
terephthalic acid and 1,6-hexanediol,
terephthalic acid, adipic acid and 1,4-butanediol,
terephthalic acid, adipic acid and ethylene glycol,
terephthalic acid, adipic acid and 1,6-hexanediol,
lactic acid and 1,4-butanediol,
lactic acid and ethylene glycol,
lactic acid and 1,6-hexanediol,
adipic acid, lactic acid and 1,4-butanediol,
adipic acid, lactic acid and ethylene glycol,
adipic acid, lactic acid and 1,6-hexanediol,
succinic acid, lactic acid and 1,4-butanediol,
succinic acid, lactic acid and ethylene glycol,
succinic acid, lactic acid and 1,6-hexanediol.

Generally, these oligomeric or polymeric esters with alcohol end groups have average degrees of polymerization from 3 to 10,000. Typically they have OH numbers of less than 100, preferably from 1 to 70, and acid numbers of less than 20, preferably less than 10.

The dihydric alcohols (a) can be used in the form of mixtures to create random polyacetals, or successively, to create block polyacetals. It is also possible to prepare block acetals by reacting divinyl ethers (b) and the dihydric alcohols (a) in a molar ratio other than 1 and then combining the resulting blocks, which carry either alcohol groups or divinyl ether groups, to form the block polyacetals. Block copolyacetals of this type are described for example in DE Application P 42 37 337.9, unpublished at the priority date of the present invention.

The dihydric alcohols may optionally be replaced by up to 50 mol % of other alcohols. Suitable for use as other alcohols are not only monohydric but also trihydric and more highly hydric alcohols. Acetaldehyde acetal polyacetals of this kind are known for example from DE Application P 4 142 130.2 and DE Application P 4 233 340.7. Polyhydric alcohols can be for example trimethylolpropane, glycerol or carbohydrates or polysaccharides, for example glucose, methylglucoside, sucrose, starch and oligofructosides such as inulin or hydrogenation products such as erythritol or sorbitol. Polyhydric alcohols can also be prepared by hydroxylation of unsaturated oils and fats. Suitable polyhydric alcohols are also obtainable by, for example, free-radically copolymerizing butanediol monovinyl ether with dimethyl maleate.

The divinyl ether component (b) comprises the divinyl ether derivatives of the alcohol component (a). Examples are butanediol divinyl ether, cyclohexanedimethanol divinyl ether and hexanediol divinyl ether.

The divinyl ethers, including divinyl ether itself, may be optionally replaced by up to 50 mol % of other vinyl ethers. Suitable for this purpose are not only monovinyl ethers and, analogously to the alcohols of components (a), vinyl ethers of polyhydric alcohols whose OH groups are completely vinylated, for example trivinyl ethers of glycerol or of trimethylolpropane.

The polyacetals can also be prepared using monovinyl ethers of the dihydric alcohols of the above-described component (a) alone. Examples are butanediol monovinyl ether, hexanediol monovinyl ether, cyclohexanedimethanol monovinyl ether.

The acetaldehyde acetal polyacetals are preferably prepared without a solvent and preferably with carboxylic acids such as oxalic acid, tartaric acid or citric acid as cationic initiator. Components (a) and (b) are preferably used in the cationically initiated polyaddition in a molar ratio from 3:2 to 2:3. The acetaldehyde acetal polyacetals have thermoplastic properties. The glass transition points of the polyacetals can be set within a wide temperature range, for example within the range from −60° to 100° C. They are for example within the range from −45° to 0° C. when using cyclohexanedimethanol divinyl ether and aliphatic diols such as butanediol or hexanediol. Such polyacetals are resinous or slow-moving sticky materials at room temperature. They can be used for coating or else as adhesive.

Polyacetals prepared from cyclic divinyl ethers and cyclic diols, for example by cationically initiated polyaddition of cyclohexanedimethanol divinyl ether and bisphenol A, have glass transition points $T_g$ within the range from 10° to 50° C.

If, in the preparation of the polyacetals, more than 1% by weight of the diols is replaced by more highly hydric alcohols, the polyacetals formed can have rubberlike properties. These polyacetals are then no longer fully soluble in diluents, only swellable. By varying components (a) and (b) it is possible to adapt the properties of the acetaldehyde acetal polyacetals to their particular end-use within wide ranges.

The acetaldehyde acetal polyacetals preferably have K values from 9 to 70 (determined by the method of H. Fikentscher in 1% solution in tetrahydrofuran at 25° C.).

The polyacetals to be used according to the present invention can be processed in the melt, as solution in organic solvents or in the form of aqueous secondary dispersions. Polyacetal melts have low viscosities at sufficiently high temperatures, for example within the range from 100° to 200° C. Such melts are castable and extrudable. Such melts are useful for example as coatings for paper and paper products. Paper products is to be understood as meaning, for example, paperboard, cardboard and bonded fiber webs. The polyacetals to be used according to the present invention are also suitable for coating films made of thermoplastics such as polyethylene, polypropylene, polyester and polyamide, films made of other compostable materials, such as starch or cellulose, and also for coating wood, fertilizers and crop protection agents.

The polymers containing acetaldehyde acetal units are soluble in organic solvents. Such solutions of polyacetals can also be used for example for preparing coatings. Examples of suitable solvents are ethyl acetate, acetone and tetrahydrofuran. Aqueous dispersions of the polyacetals to be used according to the present invention are obtained for example on dispersing the polyacetals in water at above pH 7. Such aqueous secondary dispersions are obtained for example when the polyacetals to be used according to the present invention are slurried up in water and dispersed by the action of strong shearing forces within the temperature range from 0° to 100° C. The action of ultrasound on finely divided polyacetals in aqueous suspension facilitates the dispersing. It also benefits from the addition of surfactants, salts, protective colloids and/or emulsifiers.

Solutions or secondary dispersions of the acetaldehyde acetal polyacetals can be applied by rolling, brushing, spraying or casting. Suitable substrates were mentioned above in connection with melt coating. Preference is given to coating materials which are compostable or rot. Examples of such raw materials are moldings composed of cellulose or starch.

The acetaldehyde acetal polyacetals can also be used for preparing moldings which are compostable. Moldings is here to be understood as meaning all articles which are destined for single use, for example disposable articles, such as tableware, flatware, garbage bags, agricultural harvest advancement sheeting, packaging films, and vessels for the cultivation of plants. Articles made of the polyacetals to be used according to the present invention are degraded in the presence of water and microorganisms or else only by water alone and access of air. Such materials therefore rot after a certain period under composting conditions.

The above-described moldings and coatings may optionally also be prepared from a mixture of acetaldehyde acetal polyacetals and fillers. These mixtures may contain for example from 0.5 to 99% by weight of a filler. Examples of suitable fillers are carbon black, starch, lignin powder, cellulose fibers, iron oxides, clay minerals, ores, calcium carbonate, calcium sulfate, barium sulfate and titanium dioxide. The fillers may in part also be stabilizers for the acetaldehyde acetal polyacetals, eg. calcium carbonate, sodium carbonate, sodium bicarbonate or calcium oxide. In some cases it has proved to be advantageous to mix the polyacetals to be used according to the invention with from 0.1 to 30% by weight of such alkaline fillers as are effective as stabilizer. The polyacetals to be used according to the present invention can also be given any desired color by the addition of inorganic or organic dyes. These dyes may also be deemed fillers in the widest sense. If the polyacetals to be used according to the present invention still contain vinyl ether groups, they can be covalently bonded to OH-containing coating substrates, for example to starch or cellulose, by the action of acids. Mixtures of such polyacetals and starch or cellulose are thus bonded together not just physically, but chemically. A hydrophobicization (hydrophobic modification) of starch or cellulose occurs.

Of particular interest is the use of the acetaldehyde acetal polyacetals in the form of a compostable film or coating as the outer surface of diapers. The outer diaper surface effectively seals in the urine absorbed by the fluff and optionally superabsorbent particles, based for example on crosslinked polyacrylic acid or crosslinked polyacrylamide, on the inside of the diaper. The inner surface of the diaper is usually a fiber web based on a cellulose material. The outer surface of the diapers described is biodegradable and hence compostable. It disintegrates on composting, so that the entire diaper rots, while diapers equipped with an outer layer made of polyethylene cannot be composted without prior comminution or costly removal of the polyethylene film.

The polyacetals to be used according to the present invention are also suitable for preparing composite materials, for example as bonder for adhesively bonding polyethylene films or sheets to aluminum foils or plates or for preparing composites from polyolefin films or sheets, composed of polyethylene or polypropylene, for example, and copper sheets or plates. Such adhesive bonds are water-resistant and stable in the alkaline pH range. However, they are gradually destroyed in the acid pH range. The K values of the polyacetals were determined by the method of H. Fikentscher, Cellulosechemie 13 (1932), 58–64 and 71–74. The measurements were carried out on 1% by weight solutions of the polyacetals in tetrahydrofuran at 25° C.

EXAMPLES

Preparation of Polyacetals 1

80.11 g of an isomer mixture of cyclohexanedimethanol divinyl ether are admixed with 290 mg of anhydrous oxalic acid and heated to 45° C., with stirring. After the oxalic acid has completely dissolved, the temperature of the mixture is raised to 110° C. Then 93.17 g of bisphenol A (2,2-bis(4-hydroxyphenyl)propane) are added over 1 hour a little at a time at 110°. Thereafter the reaction mixture is stirred at 90° C. for a further 72 hours, in the course of which it polymerizes. Thereafter gaseous ammonia is passed into the polyacetal melt to neutralize the oxalic acid initiator.

To prepare coatings, a 30% solution of the polyacetal in tetrahydrofuran is prepared.

EXAMPLE

A customary household bonded fiber web paper 0.1 mm in thickness is briefly dipped into the above-described polyacetal solution to coat it on both sides and air dried. The proportion of polyacetal in the coated paper is 20% by weight.

The coated paper was then immersed for 16 hours in water whose pH had been adjusted to 8 and subjected to the tensile test of DIN 53455-3. The width of the test specimen was 4 mm. The measured values of the tensile strength and breaking strength are indicated in the table.

COMPARATIVE EXAMPLE

An uncoated bonded fiber web paper 0.1 mm in thickness as described in the Example is immersed for 16 hours in water whose pH has been adjusted to 8 and then subjected to the tensile test of DIN 53455-3. The tensile and breaking strength results obtained are indicated in the table.

TABLE

|  | Tensile strength (N/mm$^2$) | Breaking strength (N/mm$^2$) |
| --- | --- | --- |
| Comparative Example | 0.34 | 0.24 |
| Example | 5.54 | 5.50 |

As is evident from the table, coating with a polyacetal which contains acetaldehyde acetal units appreciably improves not only the wet tensile strength but also the wet breaking strength of the bonded fiber web. The coated webs are watertight, ie. they do not let water through even on prolonged exposure thereto and are not attacked by water. This property of coated bonded fiber webs is of interest for using such products as outer surface of diapers.

We claim:

1. A diaper having an outer layer said outer layer comprising polyacetals containing acetaldehyde acetal units in the form of a compostable film or a compostable coating.

* * * * *